Feb. 5, 1952 F. C. RAFFEL Plant Pat. 1,071

HYBRID TEA ROSE PLANT

Filed Oct. 21, 1950

WITNESS

Addison E. Avery

INVENTOR

Frank C. Raffel

Webster & Webster

ATTYS.

Patented Feb. 5, 1952

Plant Pat. 1,071

UNITED STATES PATENT OFFICE 1,071

HYBRID TEA ROSE PLANT

Frank C. Raffel, Stockton, Calif.

Application October 21, 1950, Serial No. 191,348

1 Claim. (Cl. 47—61)

This discovery relates to a new and distinct variety of hybrid tea rose of bush type.

In particular the variety is a sport of the Charlotte Armstrong (United States Plant Patent No. 455), and was discovered by me as a branch blooming on a bush of the parent variety in my field of commercial rose stock located near Stockton, California.

As distinguished from the parent Charlotte Armstrong, which bears solid red flowers, the present variety bears rose red flowers variegated or striped with pink to pinkish white, the variegation producing a flower of unique appearance.

As further distinguished from the parent Charlotte Armstrong, the present variety bears buds and flowers which are more perfect in form when grown in cool, damp weather, and such flowers do not discolor as much as those of the present variety when subjected to rain, dew, or dampness.

A still further distinction is that the present variety is characterized by leaves which are slightly narrower than those of the parent Charlotte Armstrong.

Subsequent to its new discovery, this new variety was budded onto wild root stock, and the reproductions have been found to retain all of the characteristics of the original sport; the variety having been reproduced—preparatory to introducing the same to the trade—in my field of rose stock located as aforesaid.

Figures 1, 2:
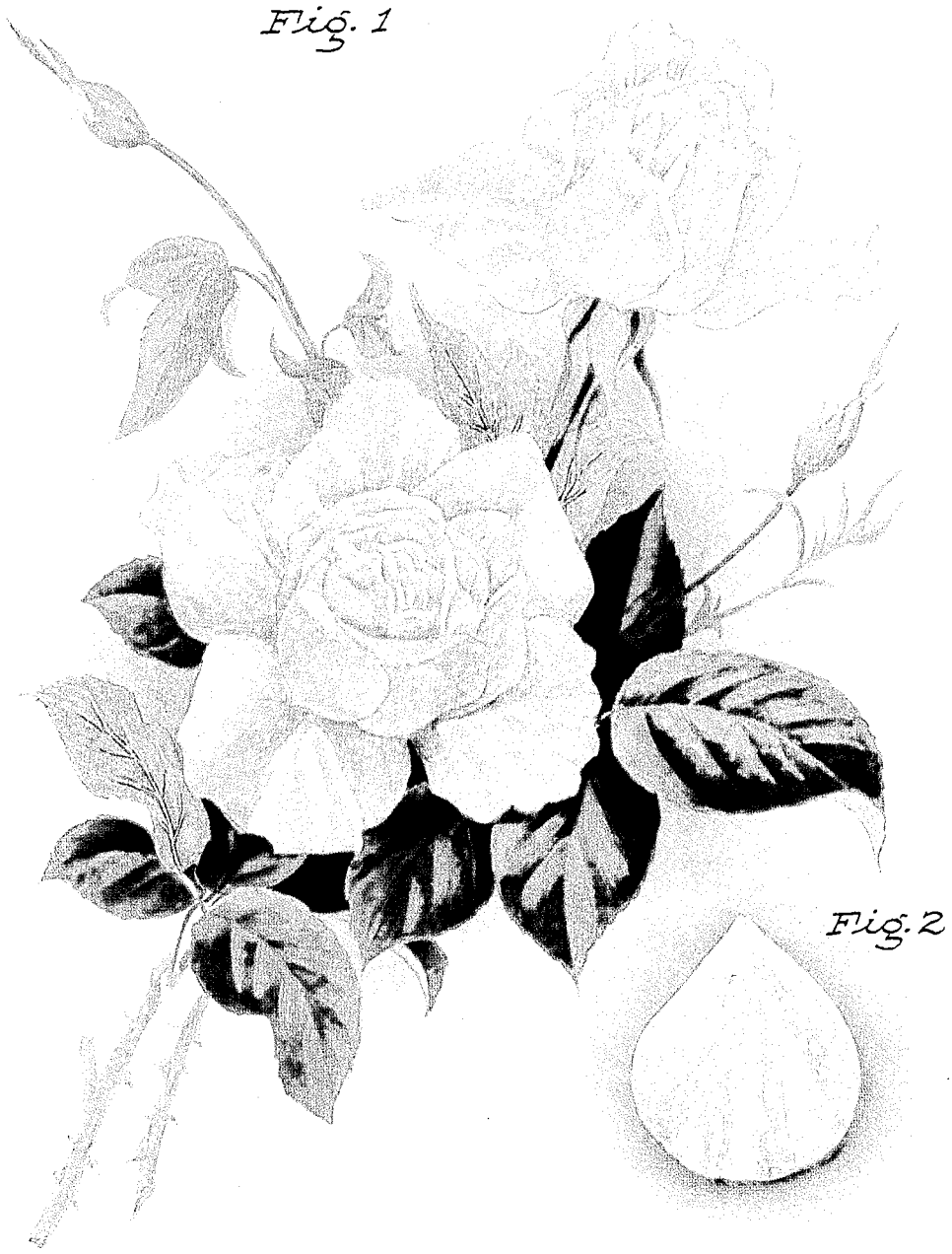
Fig. 1 is a perspective view of flowers of the rose, together with leaves and buds.
Fig. 2 is a plan view of one of the novel variegated petals of the flower.

Referring now specifically to the new and distinct variety of hybrid tea rose plant, the following is a detailed description thereof in outline; all major color plate identifications being by reference to Maerz and Paul Dictionary of Color:

Type: Bush; half hardy; sport; use—cut flowers and garden decoration.

Class: Hybrid tea.

Discovery: Sport of Charlotte Armstrong (United States Plant Patent No. 455).

*Flowers*

Continuity: Continuous during growing season.

Fragrance: Moderate.

Flowers borne: Usually singly (sometimes three or more to stem); on strong, medium length stems.

Quantity of bloom: Abundant—outdoors.

Bud: Long; slender; erect; color—yellowish green (20-L-4); almost smooth; numerous yellowish green prickles.

*Before calyx breaks.*—Size—medium. Form—pointed, with foliaceous appendages, and with slender, much cut foliaceous parts extending beyond the tip of the bud equal to three-fourths or more of its length.

*As calyx breaks.*—Color—brownish red, with few green stripes (not shown).

*As first petal opens.*—Size—large. Form—very long and pointed. Color—much the same as in full bloom, hereinafter described. Opens up well.

Bloom:

*Size.*—Large, averaging four to five inches during summer and fall, and five to six and one-half inches in spring.

*Petalage.*—Double, with from twenty-five to thirty-five petals arranged regularly.

*Form.*—Very high center; petals at first remaining very tightly rolled outward—later becoming loosely rolled outward.

Petals: Leathery, with inside satiny—outside shiny.

*Shape.*—Outside—obovate to suborbicular, usually with three notches. Intermediate—obovate, usually with three notches. Inside—obovate to cuneate, usually with three notches.

*Color.*—Rose red (49-L-5), striped pale pink (49-H-3), shading to pinkish white (49-B-1), with a distinct yellow (9-L-2) at the base. (See Fig. 2.) In general effect the flowers are colored as above, with the colors tending to bleach toward the pinkish side after the bloom is fully open.

*Behavior.*—Drop off cleanly, fade more rapidly in hot weather.

*Flower longevity.*—Bush in garden, three days in August; cut roses grown outdoors, three days in August.

Reproductive organs:

*Stamens.*—Medium number; arranged regularly about pistils; mixed with petaloids.

*Filaments.*—Medium long; yellow, with anthers.

*Anthers.*—Medium large; yellow; all open at once.

*Pollen.*—Moderate; yellow.

*Pistils.*—Medium.

*Styles.*—Uneven; medium long; thin; loosely separated.

*Stigma.*—Red to yellow at tips.

*Ovaries.*—Some protruding from calyx.

*Hips.*—Globular; pear shaped; smooth while immature; rough when mature; yellow—when half mature yellow to green on one side and yellow to brown on other side.

*Sepals.*—Permanent; very long; straight; spear shaped; color—inside: light green; outside: pale green.

*Seeds.*—Many; medium size.

*Plant*

Foliage:

*Leaves.*—Compound (of 3–5–7); many leaflets; moderately abundant; moderately large; moderately heavy; leathery.

*Leaflets.*—Acute; base rounded: margin simply serrate.

*Color.*—*Mature*—upper surface: normal green (24–L–2); under surface: light green. *Young*—upper surface: bronze red (45–G–3); under surface: light bronze red.

*Rachis.*—Light to medium; upper side: grooved; under side: sparsely prickly.

*Stipules.*—Medium length; medium width, with medium long points, turning out at an angle of more than 45°, recurved toward the stem.

*Disease.*—Fairly resistant to mildew.

Growth:

*Habit.*—Bushy; upright; much branched.

*Growth.*—Vigorous.

*Canes.*—Moderately heavy.

*Main stems.*—Brown. *Thorns*—many; medium length; hooked downward, with long broad base. *Prickles*—many; brown. *Hairs*—few; brown.

*Branches.*—Dull; green. *Thorns* — many; medium length; hooked downward, with short broad base. *Prickles*—many; brown. *Hairs*—few; brown.

*New shoots.*—Bronze. *Thorns*—many; medium length; hooked downward, with short narrow base. *Prickles* — reddish. *Hairs*—few; reddish.

The hybrid tea rose plant, and its flowers, as herein described may vary in slight detail to climatic and soil conditions under which the variety may be grown.

Having thus described my invention I claim:

A new and distinct variety of hybrid tea rose plant, substantially as described and illustrated, characterized, in comparison to the Charlotte Armstrong, by flowers having rose red petals distinctly striped pink to pinkish white, with yellow at the base of the petals; and further distinguished by buds and flowers which are more perfect in form when grown in a cool, damp climate, and by greater resistance to fading or discoloration under such conditions of growth; the plant being bush type, vigorous, and having leaves narrower than those of the Charlotte Armstrong.

FRANK C. RAFFEL.

REFERENCES CITED

The following references are of record in the file of this patent:

UNITED STATES PATENTS

| Number | Name | Date |
|---|---|---|
| Pl. P. 167 | Spandikow | Feb. 25, 1936 |
| Pl. P. 183 | Kistler | June 15, 1936 |
| Pl. P. 550 | Janssen | Oct. 13, 1942 |